United States Patent
Howard

(10) Patent No.: US 7,482,306 B2
(45) Date of Patent: Jan. 27, 2009

(54) SYNERGISTIC HERBICIDAL COMPOSITIONS COMPRISING FOMESAFEN

(75) Inventor: Scott Willie Howard, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 351 days.

(21) Appl. No.: 10/491,230

(22) PCT Filed: Oct. 2, 2002

(86) PCT No.: PCT/EP02/11089

§ 371 (c)(1), (2), (4) Date: Mar. 29, 2004

(87) PCT Pub. No.: WO03/030642

PCT Pub. Date: Apr. 17, 2003

(65) Prior Publication Data

US 2004/0242423 A1  Dec. 2, 2004

(30) Foreign Application Priority Data

Oct. 3, 2001 (CH) .................... 1821/01

(51) Int. Cl.
*A01N 43/60* (2006.01)
(52) U.S. Cl. .................... 504/136
(58) Field of Classification Search ........... 504/129, 504/130, 136, 149
See application file for complete search history.

(56) References Cited

U.S. PATENT DOCUMENTS

2002/0004457 A1 * 1/2002 Nevill et al. ............... 504/138

FOREIGN PATENT DOCUMENTS

| DE | 19851854 | 4/1999 |
|---|---|---|
| DE | 19859224 | 5/1999 |
| DE | 19915013 | 8/1999 |
| DE | 19919951 | 9/1999 |
| EP | 0023100 | 1/1981 |
| WO | 0135742 | 5/2001 |
| WO | 0152650 | 7/2001 |

OTHER PUBLICATIONS

Wesley et al. "Residual Effects of Fall Deep Tillage on Soybean Yields and Net Returns on Tunica Clay Soil" Agron. J. 92:941-947. 2000.*
Database CA 'Online—Chemical Abstract Service, Columbus, Ohio, US; Zhang, Hao et al; "Control effect of mixing of herbicides to resistant weeds on soybean field"; Database accession No. 132:218308.
Database CA 'Online, US; Little Desiree L. et al: "Postemergence combinations of fomesafen with fluazifop, bentazon, or acifluorfen, for weed control in soybeans"; Database accession No. 100:152406.
Database CA 'Online, Chemical Abstracts Service, Columbus, Ohio, US; Fontes, Jose Roberto Antoniol et al: "Effects of herbicides on weed control on mungbean"Vigna radiata (L.) Wilczek!; Database Accession No. 137:347836.
Database CA 'Online, Chemical Abstracts Service, Columbus, Ohio, Da Silva, Wilson et al: "Alfalfa (Medicago pre-emergence and post-emergence herbicides"; Database Accession No. 136:336595.
Database CA 'Online, Chemical Abstracts Service, Columbus, Ohio; Novo, M.C.S.S. et al: "Post-emergence herbicides effect on plant growth and symbiotic nitrogen fixation for peanut"; Database Accession No. 130:193031.
Database CA 'Online, Chemical Abstracts Service, Columbus, Ohio, US; Ozair, Chaudhry A. et al.: "Performance of herbicides in spring and autumn planted soybean"; Database Accession No. 12:29144.

* cited by examiner

*Primary Examiner*—Alton N Pryor
(74) *Attorney, Agent, or Firm*—Rebecca A. Howard

(57) ABSTRACT

A herbicidal synergistic composition for the control of weeds and grasses in protoporphyrinogen-oxidase-inhibitor-resistant crops of useful plants which, in addition to comprising customarily inert formulation adjuvants, comprises as active ingredients a) a herbicidally effective amount of 5-[2-chloro-4-(trifluoromethyl)phenoxy]-N-(methylsulfonyl)-2-nitrobenzamide of formula (1) which inhibits the action of protoporphyrinogen oxidases, and b) a synergistically effective amount of at least one further compound selected from the group consisting of the co-herbicides diclosulam, foramsulfuron, tepraloxydim, fluazifop-butyl I and fluazifop-P-butyl.

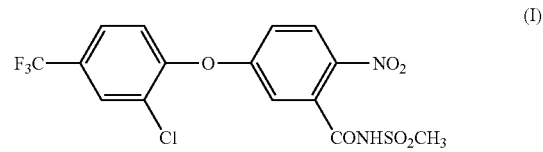

(I)

6 Claims, No Drawings

SYNERGISTIC HERBICIDAL COMPOSITIONS COMPRISING FOMESAFEN

"This application is a 371 of International Application No. PCT/EP02/11089 filed Oct. 2, 2002, which claims priority to CH 1821/01, filed Oct. 3, 2001, the contents of which are incorporated herein by reference."

The present invention relates to a novel herbicidal synergistic composition comprising a herbicidal active ingredient combination that is suitable for the selective control of undesired plant growth in protoporphyrinogen-oxidase-inhibitor-resistant crops of useful plants, for example maize, sugar beet, rape, cotton, sunflowers, cereals, rice, sugar cane and, especially, soybeans.

The invention relates also to a method of controlling undesired plant growth, using the herbicidal composition, and to the use of the said composition for that purpose.

Active ingredients that come into consideration are a) 5-[2-chloro-4-(trifluoromethyl)-phenoxy]-N-(methylsulfonyl)-2-nitro-benzamide, which inhibits the action of protoporphyrinogen oxidases in plants (=protoporphyrinogen oxidase inhibitors), and b) at least one further co-herbicide selected from the group diclosulam, foramsulfuron, tepraloxydim, fluazifop-butyl and fluazifop-P-butyl.

The herbicides under a) and b) are known and described, for example, in 'The Pesticide Manual', Editor C. D. S. Tomlin, 12th Edition, British Crop Protection Council, 2000 or are known under the CAS Registry Number (CAS Reg. No.).

WO 98/33927, WO 98/29554, WO 01/12825, WO 01/36606, U.S. Pat. Nos. 5,767,373, 5,939,602 and 6,084,155 describe genetically transformed plants that are resistant to certain herbicides that inhibit protoporphyrinogen biosynthesis. The genetically transformed useful plants described therein and the methods for the production thereof are to be considered part of the present disclosure.

Surprisingly, it has now been found that a combination of variable amounts of protoporphyrinogen-oxidase-inhibiting active ingredient under a) with one or more of the herbicidal active ingredients listed under b), all of which are known and most of which are also commercially available, exhibits a synergistic action that is capable of controlling, both pre-emergence and post-emergence, the majority of weeds and grasses occurring especially in protoporphyrinogen-oxidase-inhibitor-resistant crops of useful plants, without causing any appreciable damage to the useful plant.

There is therefore proposed in accordance with the present invention a novel synergistic composition for the selective control of weeds and grasses in protoporphyrinogen-oxidase-inhibitor-resistant crops of useful plants which, in addition to comprising customary inert formulation adjuvants, comprises as active ingredient a mixture of a) a herbicidally effective amount of 5-[2-chloro-4-(trifluoromethyl)phenoxy]-N-(methyl-sulfonyl)-2-nitro-benzamide of formula I

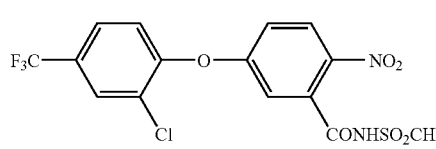

(I)

which inhibits the action of protoporphyrinogen oxidases, and b) a synergistically effective amount of at least one further compound selected from the group consisting of the co-herbicides diclosulam, foramsulfuron, tepraloxydim, fluazifop-butyl and fluazifop-P-butyl.

The compound of formula I is known as a herbicide under the common name fomesafen and is described, for example, in 'The Pesticide Manual', 12th Edition, British Crop Protection Council, 2000, under entry number (391).

Likewise, the co-herbicides under b), diclosulam (235), tepraloxydim (735), fluazifop-butyl (352) and fluazifop-P-butyl (353), are described, for example, in 'The Pesticide Manual', 12th Edition, Editor C. D. S. Tomlin, British Crop Protection Council, 2000, under the entry numbers added in brackets; for example diclosulam (235) is described therein under entry number 235.

Foramsulfuron is known under the designation AEF130360 and the CAS Registry Number (Reg. No.) [173159-57-4] and corresponds to the compound N,N-dimethyl-2-[[N-[[N-(4, 6-dimethoxypyrimidin-2-yl)amino]carbonyl]amino]sulfonyl]-4-formamidobenzamide.

Fomesafen may occur both in protonated form and in the form of salts, e.g. in the form of a sodium salt. Where mention is made of the herbicides, all customary derivatives, for example as mentioned especially in the said 'Pesticide Manual' or any other reference source, are to be considered part of the present disclosure.

Preferred herbicidal synergistic compositions for the control of weeds and grasses in protoporphyrinogen-oxidase-inhibitor-resistant crops comprise the following specific active ingredient combinations: compound of formula I+diclosulam; compound of formula I+foramsulfuron; compound of formula I+tepraloxydim; compound of formula I+fluazifop-butyl; compound of formula I+fluazifop-P-butyl; compound of formula I+tepraloxydim+fluazifop-butyl; and compound of formula I+tepraloxydim+fluazifop-P-butyl.

It is extremely surprising that the combination of the protoporphyrinogen-oxidase-inhibiting active ingredient under a) with at least one active ingredient selected from the co-herbicides under b) exceeds the additive action on the weeds to be controlled that is to be expected in principle and thus broadens the range of action of the individual active ingredients especially in two respects: firstly, the rates of application of the individual compounds a) and b) are reduced while a good level of action is maintained and, secondly, the composition according to the invention achieves a high level of weed control also in those cases where the individual substances, in the range of low rates of application, have become useless from the agronomic standpoint. The result is a considerable broadening of the spectrum of weeds, as is necessary and desirable in the event of an unintentional overdose of active ingredient. The composition according to the invention, while retaining excellent control of weeds in protoporphyrinogen-oxidase-inhibitor-resistant useful plants, also allows greater flexibility in succeeding crops.

The composition according to the invention can be used against a large number of agronomically important weeds, such as *Stellaria, Nasturtium, Agrostis, Digitaria sanguinalis, Avena, Setaria* spp., *Datura stramonium, Eriochloa villosa, Polygonum* spp., *Cassia obtusifolia, Ambrosia* spp., *Helianthus* spp., *Apocynum sibiricum, Convolvulus arvensis, Cirsium arvense, Setaria lutescens, Setaria viridis, Sinapis, Lolium, Brachiaria* spp., *Eleusine indica, Panicum* spp., *Abutilon theophrasti, Bidens pilosa, Euphorbia* spp., *Portulaca oleracea, Tagetes minuta, Asclepia* spp., *Solanum nigrum, Phaseolus, Echinochloa crus galli, Scirpus, Sagittaria, Bromus, Alopecurus, Sorghum* spp., *Cyperus* spp., *Abutilon, Sida spinosa, Xanthium strumarium, Amaranthus* spp., *Chenopodium album, Ipomoea* spp., Chrysanthemum and 'volunteer cereals' such as, for example wild-growing cereals and maize. The composition according to the invention is suitable for all methods of application conventionally used in agriculture, e.g. pre-emergence application, post-emergence application and seed dressing. The composition according to the invention is suitable especially for controlling weeds in protoporphyrinogen-oxidase-inhibitor-resistant crops of useful plants, for example maize, sugar beet, rape, cotton, sunflowers, cereals, rice, sugar cane and, especially, soybeans. Such useful plants and their production are described, for example, in WO 95/34659 and WO 98/33927.

The composition according to the invention comprises the protoporphyrinogen oxidase inhibitor a) and the co-herbicide b) in any mixing ratio, but usually has an excess of one component over the other. Preferred mixing ratios of the active ingredient a) to the co-herbicide b) are from 1:2000 to 2000:1, especially from 1:200 to 200:1.

The rate of application may vary within wide limits and depends on the nature of the soil, the method of application (pre- or post-emergence; seed dressing; application to the seed furrow; no tillage application etc.), the crop plant, the weed to be controlled, the prevailing climatic conditions, and other factors governed by the method of application, the time of application and the target crop. The active ingredient mixture according to the invention can generally be applied at a rate of from 1 to 5000 g of active ingredient mixture per ha, especially from 1 to 2000 g of active ingredient per ha.

The invention relates also to a method of selectively controlling weeds and grasses in protoporphyrinogen-oxidase-inhibitor-resistant crops of useful plants, which comprises treating the useful plants, seeds or cuttings thereof, or the area of cultivation thereof, simultaneously or separately with an amount, effective for herbicide synergy, of the herbicide a) and at least one further co-herbicide b).

Preference is given to a method in which the herbicide a) is applied to protoporphyrinogen-oxidase-inhibitor-resistant useful plants, especially soybeans, or to the area surrounding those useful plants and, together with the herbicide a) or at a later time, a further co-herbicide b) or, optionally, a mixture of such substances, is applied. The active ingredients that come into consideration as herbicide a) and co-herbicides b) are the same active ingredients as those mentioned hereinabove.

The mixtures of the protoporphyrinogen oxidase inhibitor a) with the co-herbicides b) may be used in unmodified form, that is to say as obtained in synthesis. Preferably, however, they are formulated in customary manner, together with the adjuvants conventionally used in formulation technology, such as solvents, solid carriers or surfactants, for example into emulsifiable concentrates, directly sprayable or dilutable solutions, dilute emulsions, wettable powders, soluble powders, dusts, granules or microcapsules, as described in WO 97/34483, pages 9 to 13. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the protoporphyrinogen oxidase inhibitor a) and the co-herbicides b), and also, where appropriate, one or more solid or liquid formulation adjuvants, are prepared in a manner known per se, e.g. by intimately mixing and/or grinding the active ingredients with the formulation adjuvants, e.g. solvents or solid carriers. In addition, surface-active compounds (surfactants) may also be used in the preparation of the formulations.

Examples of solvents and solid carriers are given, for example, in WO 97/34485, page 6.

Depending on the nature of the active ingredient of formula I under a) and the co-herbicides under b) to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, in WO 97/34485, pages 7 and 8.

Also suitable for the preparation of the herbicidal compositions according to the invention are the surfactants conventionally employed in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, MunichNienna, 1981 and M. and J. Ash, "Encyclopedia of Surfactants", Vol I-III, Chemical Publishing Co., New York, 1980-81.

The herbicidal formulations usually contain from 0.1 to 99% by weight, especially from 0.1 to 95% by weight, of active ingredient mixture comprising the compound under a) together with the co-herbicides under b), from 1 to 99.9% by weight of a solid or liquid formulation adjuvant, and from 0 to 25% by weight, especially from 0.1 to 25% by weight, of a surfactant.

Whereas commercial products are usually formulated as concentrates, the end user will normally employ dilute formulations. The compositions may also comprise further ingredients, such as stabilisers, e.g. vegetable oils or epoxidised vegetable oils (epoxidised coconut oil, rapeseed oil or soybean oil), antifoams, e.g. silicone oil, preservatives, viscosity regulators, binders, tackifiers, and also fertilisers or other active ingredients. Preferred formulations have especially the following compositions:

(%=percent by weight)

Emulsifiable Concentrates:
    active ingredient mixture: 1 to 90%, preferably 5 to 20%
    surfactant: 1 to 30%, preferably 10 to 20%
    liquid carrier: 5 to 94%, preferably 70 to 85%

Dusts:
    active ingredient mixture: 0.1 to 10%, preferably 0.1 to 5%
    solid carrier: 99.9 to 90%, preferably 99.9 to 99%

Suspension Concentrates:
    active ingredient mixture: 5 to 75%, preferably 10 to 50%
    water: 94 to 24%, preferably 88 to 30%
    surfactant: 1 to 40%, preferably 2 to 30%

Wettable Powders:
    active ingredient mixture: 0.5 to 90%, preferably 1 to 80%
    surfactant: 0.5 to 20%, preferably 1 to 15%
    solid carrier: 5 to 95%, preferably 15 to 90%

Granules:
    active ingredient mixture: 0.1 to 30%, preferably 0.1 to 15%
    solid carrier: 99.5 to 70%, preferably 97 to 85%

The following Examples illustrate the invention further, but do not limit the invention.

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |

| F1. Emulsifiable concentrates | a) | b) | c) | d) |
|---|---|---|---|---|
| octylphenol polyglycol ether (7-8 mol of ethylene oxide) | — | 4% | — | 2% |
| cyclohexanone | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredients (or the active ingredient mixture) are mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredients (or the active ingredient mixture) are dissolved in methylene chloride and applied to the carrier by spraying, and the solvent is then evaporated off in vacuo.

| F5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredients (or the finely ground active ingredient mixture) are uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredients (or the active ingredient mixture) are mixed and ground with the adjuvants, and the mixture is moistened with water. The mixture is extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredients (or the active ingredient mixture) with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredients (of the finely ground active ingredient mixture) are intimately mixed with the adjuvants, giving a suspension concentrate from which suspensions of any desired concentration can be obtained by dilution with water.

It is often more practical for the active ingredient under a) and the mixing partner or partners under b) to be formulated separately and to be brought together in the desired mixing ratio in the applicator in the form of a "tank mixture" in water shortly before application.

BIOLOGICAL EXAMPLES

A synergistic effect exists whenever the action of the combination of active ingredients a) and b) is greater than the sum of the actions of the active ingredients applied separately.

The herbicidal action to be expected We for a given combination of two herbicides can be calculated according to COLBY, S. R., "Calculating synergistic and antagonistic response of herbicide combinations", Weeds 15, pages 20-22, 1967:

$$We = X + [Y \cdot (100-X)/100]$$

wherein:

X=percentage herbicidal action on treatment with the compound of formula I at a rate of application of p kg per hectare, compared with the untreated control (=0%).

Y=percentage herbicidal action on treatment with a co-herbicide under b) at a rate of application of q kg per hectare, compared with the untreated control.

We=expected herbicidal action (percentage herbicidal action compared with the untreated control) following treatment with the compound of formula I under a) and co-herbicide under b) at a rate of application of p+q kg of active ingredient per hectare.

When the action actually observed is greater than the value to be expected We, there is a synergistic effect.

The synergistic effect of the combinations of the active ingredient under a) with the co-herbicide active ingredients under b) is demonstrated in the following Examples.

Example B1

Pre-Emergence Test

Monocotyledonous and dicotyledonous test plants are sown in pots under greenhouse conditions. A standard soil is used as cultivation substrate. At a pre-emergence stage, the herbicides are applied alone and in the form of a mixture to the soil surface. The application is carried out using an aqueous suspension of the test compounds prepared from a 25% suspension concentrate (Example F8, c)), using 500 litres of water/ha. The rates of application depend on the optimum concentrations ascertained under field conditions or greenhouse conditions. The test plants are then cultivated in the greenhouse under optimum conditions. The tests are evaluated after from 1 to 4 weeks (% action, 100%=plant has died, 0%=no phytotoxic action).

The mixtures used in this test exhibit good synergistic effects.

Example B2

Post-Emergence Test

The test plants are grown in pots under greenhouse conditions to a post-application stage (3- to 4-leaf stage). A standard soil is used as cultivation substrate. At the 3- to 4-leaf stage, the herbicides are applied alone and in the form of a mixture to the test plants. The application is carried out using an aqueous suspension of the test compounds prepared from a 25% suspension concentrate (Example F8, c)), using 200 litres of water/ha. The rates of application depend on the optimum concentrations ascertained under field conditions or greenhouse conditions. The tests are evaluated after from 1 to 4 weeks (% action, 100%=plant has died, 0%=no phytotoxic action).

The mixtures used in this test also exhibit good synergistic effects.

What is claimed is:

1. A herbicidal synergistic composition for the selective control of weeds and grasses in protoporphyrinogen-oxidase-inhibitor-resistant crops of useful plants, comprising:
   (A) fomesafen in an amount sufficient to inhibit protoporphyrinogen oxidases of said weeds and grasses; and
   (B) a synergistically effective amount of diclosulam.

2. The herbicidal synergistic composition according to claim 1 wherein the weight ratio of said fomesafen to said dicosulam is a range from 1:2000 to 2000:1.

3. A herbicidal synergistic composition according to claim 1 including selected inert formulation adjuvants.

4. A method of controlling the growth of weeds and grasses in protoporphyrinogen-oxidase-inhibitor-resistant crops of useful plants, comprising treating said useful plants, or seeds or cuttings thereof, or the area of cultivation thereof, with an effective amount of a herbicidal synergistic composition wherein said composition includes a mixture of:
   (A) fomesafen in an amount sufficient to inhibit protoporphyrinogen oxidases of said weeds and grasses; and
   (B) a synergistically effective amount of diclosulam.

5. A method according to claim 4 wherein said protoporphyrinogen-oxidase-inhibitor-resistant crops are soybean crops.

6. The method according to claim 4 wherein said herbicidal synergistic composition is applied at an application rate of from 1 gram to 5000 grams per hectare.

* * * * *

UNITED STATES PATENT AND TRADEMARK OFFICE
CERTIFICATE OF CORRECTION

PATENT NO. : 7,482,306 B2
APPLICATION NO. : 10/491230
DATED : January 27, 2009
INVENTOR(S) : Stott Willie Howard Page 1 of 1

It is certified that error appears in the above-identified patent and that said Letters Patent is hereby corrected as shown below:

Title Page, item [75] the Inventor should read as follows: Stott Willie Howard

Signed and Sealed this

Seventeenth Day of March, 2009

JOHN DOLL
*Acting Director of the United States Patent and Trademark Office*